US00PP27866P3

(12) United States Plant Patent
Rayner

(10) Patent No.: US PP27,866 P3
(45) Date of Patent: Apr. 11, 2017

(54) MANGO TREE NAMED 'RA/17'

(50) Latin Name: *Mangifera indica*
Varietal Denomination: RA/17

(71) Applicant: Kenneth Rayner, Katherine (AU)

(72) Inventor: Kenneth Rayner, Katherine (AU)

( * ) Notice: Subject to any disclaimer, the term of this patent is extended or adjusted under 35 U.S.C. 154(b) by 36 days.

(21) Appl. No.: 14/544,769

(22) Filed: Feb. 13, 2015

(65) Prior Publication Data

US 2016/0242333 P1 Aug. 18, 2016

(51) Int. Cl.
*A01H 5/08* (2006.01)

(52) U.S. Cl.
USPC ..... Plt./159

(58) Field of Classification Search
USPC ..... Plt./156, 159
See application file for complete search history.

(56) References Cited

PUBLICATIONS

Plant Variety Journal: Offical Journal of Plant Breeder's Rights Office. vol. 24: 4. 2012. 12 pages.*

Mango Matters. 2014. vol. 15. retrieved on Nov. 30, 2016, retrieved from the Internet at (https://static1.squarespace.com/static/53b0ef57e4b04ed3debabc4f/t/53eb11d7e4b09c55b3b01711/1407914455144/Mango+Matters+Autumn+-+Final+%28Interactive%29.pdf). 3 pages.*

* cited by examiner

*Primary Examiner* — June Hwu
*Assistant Examiner* — Karen Redden
(74) *Attorney, Agent, or Firm* — Michelle Bos Legal LLC

(57) ABSTRACT

A new mango tree named 'RA/17', distinguished by its attractive fruit having excellent flavor and a long shelf life.

3 Drawing Sheets

Genus and species: *Mangifera indica.*
Variety denomination: 'RA/17'.

CROSS-REFERENCE TO RELATED APPLICATIONS

None

BACKGROUND AND SUMMARY OF THE VARIETY

The new mango tree 'RA/17' originated as a controlled cross of 'Irwin' (female parent, not patented) and 'R2E2' (male parent, not patented). The initial cross was made at Katherine, Northern Territory, Australia in 1996, and seedlings resulting from the cross were planted in 1997 in the same location. 'RA/17' was selected from among the seedlings for further observation due to its attractive fruit having excellent flavor and a long shelf life. In 2006, 'RA/17' was asexually propagated by grafting at Katherine, Northern Territory, Australia, and has since been observed to reproduce true to type over successive asexually propagated generations.

'RA/17' is distinguishable from its parents by the following characteristics:

TABLE 1

| | 'RA/17' | 'Irwin' | 'R2E2' |
|---|---|---|---|
| Tree shape | Upright, open canopy | Upright, semi-open canopy | Upright, open canopy |
| Shape of dorsal shoulder in mature fruit | Rounded outward | Rounded downward | |

TABLE 1-continued

| | 'RA/17' | 'Irwin' | 'R2E2' |
|---|---|---|---|
| Fruit size | Medium, 375 g to 560 g | Small, 262 g | Large, 600 to 1000 g |
| Fruit maturity | Early season | Mid-season | Mid- to late-season |

'RA/17' matures earlier than known varieties 'Honey Gold' (not patented) and 'Van Dyke' (not patented), both of which are considered late maturing varieties.

BRIEF DESCRIPTION OF THE PHOTOGRAPHS

Figure 1:
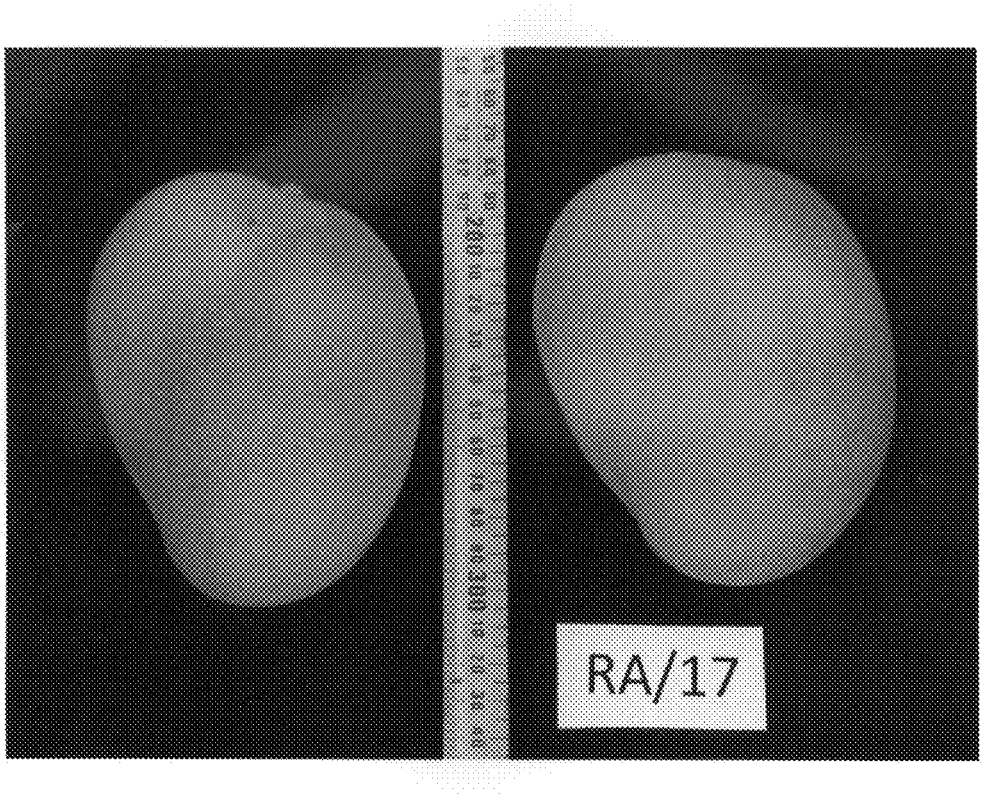
FIG. 1 shows edible ripe fruit of the 'RA/17' variety.
Figure 2:
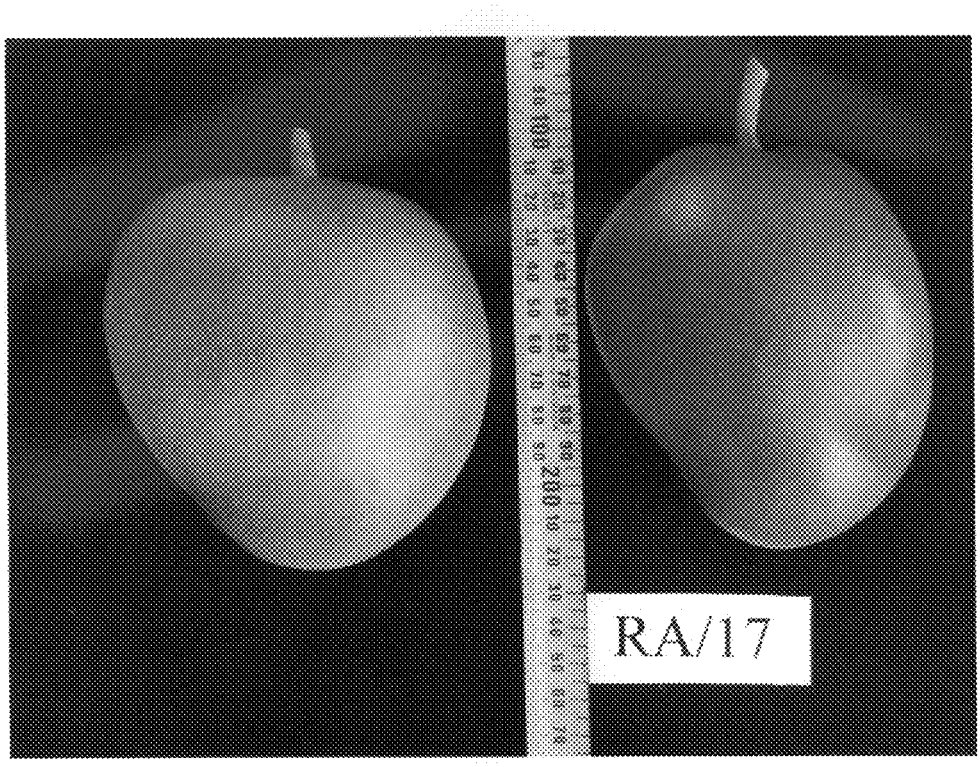
FIG. 2 shows green mature fruit of the 'RA/17' variety, ready for packing and transport; and, FIG. 3 shows a three-year-old tree of the 'RA/17' variety.
Figure 3:
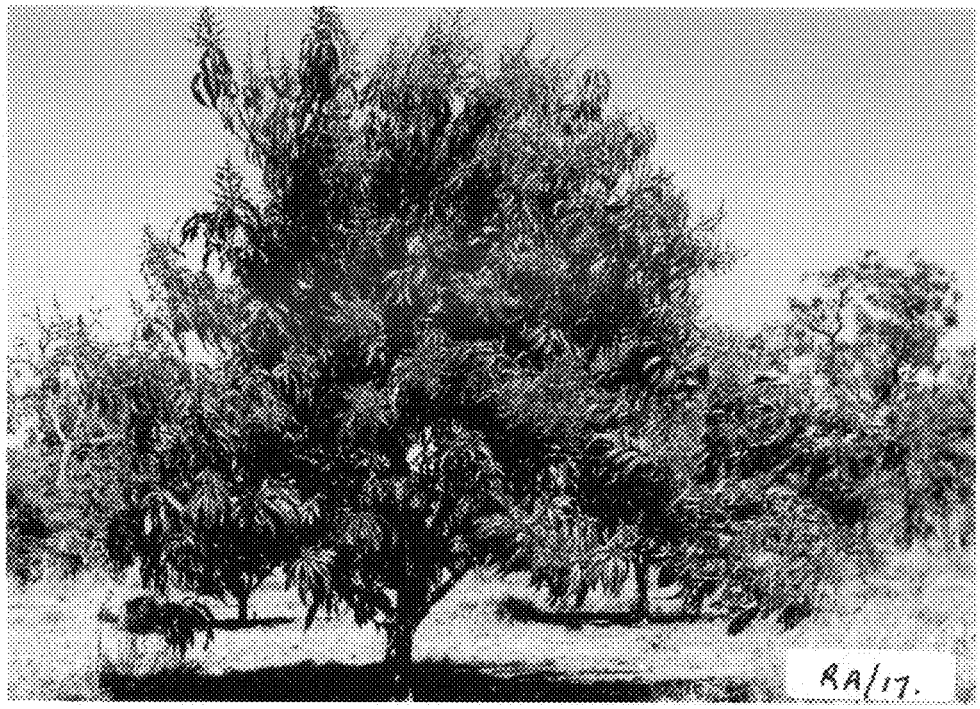

The colors of the claimed variety may vary with lighting conditions. Color characteristics of the variety should therefore be determined with reference to the observations described herein, rather than from these illustrations alone.

DETAILED BOTANICAL DESCRIPTION

The following detailed botanical description is based on observations of trees planted in 2009 and grown on 'Kensington Pride' rootstock (not patented). Observations were recorded and photographs taken during the 2009 through 2012 growing seasons at Berry Springs, Northern Territory, Australia. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants of the new variety may vary from the stated average. Colors are described with reference to The Royal Horticultural Society Mini Colour Chart (2007).

Tree:

*Vigor*.—Vigorous.
*Height*.—Up to about 7.5 m.
*Spread*.—Up to about 6 m.
*Growth habit*.—Narrow upright, open canopy.
*Productivity*.—Good to very good; regular bearer.
*Trunk diameter*.—29 cm at 60 cm above soil line.
*Bark texture*.—Rough.
*Bark color*.—Grey-brown 199C.

Branches:

*Bark color*.—Old wood — grey-brown 199C; one-year-old wood — dark green.
*Bark texture*.—Slightly rough.

Inflorescence:

*Number of years to first flowering*.—Seedling — 5 years; Graft — 2 years.
*Regularity of flowering*.—Very regular.
*Form*.—Panicle.
*Inflorescence position*.—Terminal.
*Axis growth habit*.—Erect to drooping.
*Shape*.—Broadly pyramidal.
*Length*.—25 cm to 35 cm.
*Width*.—25 to 30 cm.
*Color*.—Red.
*Peduncle*.—Length 6 mm, red.
*Pubescence*.—None.
*Leafy bracts*.—Present some seasons; length 19 mm, width 13 mm, glabrous.
*Buds*.—Burst timing similar to 'Irwin'; flowering lasts 25 to 35 days, varies by season; diameter 3 mm; yellow-green 146C, shape pyramidal.
*Density of flowers*.—Very dense, up to 2000 flowers per panicle.
*Type of flower*.—Pentamerous.
*Flower size*.—Diameter 5 mm to 7 mm.
*Fragrance*.—Pungent.
*Flower color*.—White 155A with yellow throat that turns pink with age; pubescent.
*Pedicel*.—Length 3 mm; red.
*Stamen*.—Usually one.
*Anther*.—Red; pollen is grey after dehiscence.
*Pollinator*.—Not required.

Leaves:

*Length*.—28 cm.
*Width*.—4.8 cm.
*Margin*.—Entire, undulate.
*Pubescence*.—None.
*Color—young leaf*.—Upper surface — Green 136A. Lower surface — Green 165A.
*Color—mature leaf*.—Upper surface — Green 137A. Lower surface — Green 137C.
*Leaf shape*.—Oblanceolate.
*Venation*.—Primary central vein with herringbone side veins.
*Apex shape*.—Acuminate.
*Base shape*.—Cuneate.
*Petiole length*.—5 cm.
*Petiole diameter*.—3 mm.
*Petiole color*.—Yellow-green 144A.
*Leaf orientation*.—Petiole semi-erect, leaf drooping.
*Leaf arrangement*.—Random spiral.

Fruit:

*Weight*.—375 g to 560 g.
*Length*.—120 mm.
*Diameter*.—90 mm.
*Relative size*.—Medium.
*Apex*.—Obtuse.
*Form of shoulder*.—Rounded outwards, sloping abruptly.
*Form of stalk cavity*.—Shallow.
*Stalk attachment*.—Immature fruit — square on; mature fruit — recessed.
*Stalk*.—Length 25 mm, diameter 9 mm tapering to 4 mm; greyed-red 179A.
*Beak*.—Not present.
*Stylar scar*.—Usually absent; sometimes just visible.
*Skin*.—Tough, thick.
*Skin color of immature fruit*.—Green 131D; with direct sunlight, red 39B blush.
*Skin color of mature fruit*.—Ground color orange 24A with red 41A blush.
*Flesh texture*.—Fine, very firm and juicy.
*Flesh color*.—Orange 24A.
*Sweetness*.—14 to 17 Brix.
*Fiber*.—None.
*Aroma*.—Mild, pleasant.
*Fruit per panicle*.—1 to 4.

Stone:

*Length*.—10 cm.
*Width*.—5 cm.
*Depth*.—4.8 cm.
*Venation*.—Weak.
*Texture of stone fiber*.—Fine.
*Adherence of fiber to stone*.—Weak.
*Color*.—White 155A.
*Embryony*.—Mono-embryonic.
*Storage*.—Up to four weeks in a home refrigerator.
*Susceptibility to bruising*.—Slight.
*Susceptibility to disease*.—Slight.
*Relative harvest maturity*.—Early, October 22 to Nov. 20, 2016, varies by year.
*Use*.—Fresh market.
*Drought, heat and cold tolerance*.—Tolerant in area grown (Berry Springs, Northern Territory, Australia).

I claim:

1. A new and distinct variety of mango tree, substantially as illustrated and described herein.

* * * * *